United States Patent
Kim et al.

(10) Patent No.: US 12,303,579 B2
(45) Date of Patent: May 20, 2025

(54) COSMETIC COMPOSITION FOR BLOCKING ULTRAVIOLET AND INFRARED RAYS

(71) Applicant: COSMAX, INC., Hwaseong-si (KR)

(72) Inventors: Su Ji Kim, Seongnam-si (KR); Jun Bae Lee, Seongnam-si (KR); Hyung Taek Lim, Seongnam-si (KR); Yong Seok Jeon, Seongnam-si (KR); Myeong Sam Park, Seongnam-si (KR)

(73) Assignee: COSMAX, INC., Hwaseong-si (KR)

( * ) Notice: Subject to any disclaimer, the term of this patent is extended or adjusted under 35 U.S.C. 154(b) by 708 days.

(21) Appl. No.: 17/614,102

(22) PCT Filed: Mar. 31, 2020

(86) PCT No.: PCT/KR2020/004423
§ 371 (c)(1),
(2) Date: Nov. 24, 2021

(87) PCT Pub. No.: WO2020/242033
PCT Pub. Date: Dec. 3, 2020

(65) Prior Publication Data
US 2022/0218577 A1    Jul. 14, 2022

(30) Foreign Application Priority Data
May 29, 2019    (KR) .................. 10-2019-0063306

(51) Int. Cl.
| | |
|---|---|
| *A61K 8/29* | (2006.01) |
| *A61K 8/36* | (2006.01) |
| *A61K 8/365* | (2006.01) |
| *A61K 8/37* | (2006.01) |
| *A61Q 17/04* | (2006.01) |
| *A61Q 19/08* | (2006.01) |

(52) U.S. Cl.
CPC .............. *A61K 8/29* (2013.01); *A61K 8/361* (2013.01); *A61K 8/365* (2013.01); *A61K 8/375* (2013.01); *A61Q 17/04* (2013.01); *A61Q 19/08* (2013.01); *A61K 2800/412* (2013.01); *A61K 2800/5922* (2013.01)

(58) Field of Classification Search
None
See application file for complete search history.

(56) References Cited

U.S. PATENT DOCUMENTS

| 8,647,609 | B2 | 2/2014 | Kim et al. |
| 9,480,632 | B2 | 11/2016 | Yi et al. |
| 10,456,350 | B2 | 10/2019 | Jang et al. |
| 2012/0015015 | A1* | 1/2012 | Kim ............... A61Q 17/04 424/59 |

FOREIGN PATENT DOCUMENTS

| JP | 2012511499 A | 5/2012 |
| JP | 2012184178 A | 9/2012 |
| JP | 2013194041 A | 9/2013 |
| JP | 2017523150 A | 8/2017 |
| JP | 2017171655 A | 9/2017 |
| JP | 2018104401 A | 7/2018 |
| KR | 20110010553 A | 2/2011 |
| KR | 101061289 B1 | 8/2011 |
| KR | 20160144779 A | 12/2016 |
| KR | 20190022340 A | 3/2019 |
| WO | 2010068687 A1 | 6/2010 |

OTHER PUBLICATIONS

Notice of Reasons for Refusal, dated Dec. 8, 2022, issued in corresponding Japanese Patent Application No. 2021-569911, including English language translation, 6 pps.
Notice of Reasons for Refusal, dated Jun. 8, 2023, issued in corresponding Japanese Patent Application No. 2021-569911, including English language translation, 8 pgs.
Notice of Allowance issued by the Korean Intellectual Property Office in corresponding Korean Patent Application No. 10-2019-0063306 on Dec. 1, 2020.
Office Action issued by the Korean Intellectual Property Office in corresponding Korean Patent Application No. 10-2019-0063306 on Jul. 28, 2020.
Office Action issued by the Korean Intellectual Property Office in corresponding Korean Patent Application No. 10-2019-0063306 on Mar. 3, 2020.
Rejection Decision issued by the Korean Intellectual Property Office in corresponding Korean Patent Application No. 10-2019-0063306 on Sep. 21, 2020.
International Search Report (PCT/ISA/210) with translation and Written Opinion (PCT/ISA/237) mailed on Jun. 24, 2020, by the Korean Patent Office as the International Searching Authority for International Application No. PCT/KR2020/004423. (9 pages).

* cited by examiner

*Primary Examiner* — Melissa S Mercier
(74) *Attorney, Agent, or Firm* — Panitch Schwarze Belisario & Nadel LLP

(57) ABSTRACT

Provided is a cosmetic composition for blocking infrared rays and ultraviolet rays at the same time, the cosmetic composition including an inorganic material which blocks ultraviolet rays, an inorganic material which blocks infrared rays, and a dispersing agent.

5 Claims, 1 Drawing Sheet

ULTRAVIOLET RAY-BLOCKING MATERIAL

NEAR-INFRARED RAY-BLOCKING MATERIAL

COSMETIC COMPOSITION FOR BLOCKING ULTRAVIOLET AND INFRARED RAYS

TECHNICAL FIELD

The present disclosure relates to a cosmetic composition for blocking ultraviolet and infrared rays at the same time.

BACKGROUND ART

Skin aging may be divided into intrinsic aging caused by passage of time and photoaging caused by long-term exposure to sunlight. Intrinsic aging is an inevitable aging phenomenon that naturally occurs with aging, whereas photoaging is a phenomenon that occurs due to prolonged exposure to sunlight, and causes skin changes such as loss of elasticity, deep wrinkles, pigmentation, etc. In addition, photoaging is very important in preventing skin aging because it develops more rapidly than intrinsic aging.

The sunlight reaching the earth's surface is broadly classified into infrared rays, visible rays, and ultraviolet rays. Among them, UV rays cause skin aging, and the dangers of this have been well known for a long time. Therefore, to protect the skin from ultraviolet rays, various products using UV-blocking organic/inorganic materials are being developed. However, not only ultraviolet rays but also infrared rays, particularly, near-infrared rays (760 nm to 1400 nm), which penetrate into the epidermis and dermis to cause skin aging, have also recently been recognized as one of the main factors of skin aging. Accordingly, many studies on infrared rays and skin aging are being reported. For this reason, there is a growing interest in the development of infrared ray-blocking products.

Ultraviolet ray-blocking materials may be classified into organic materials and inorganic materials. Organic materials may be applied to various formulations in a way that absorbs and blocks ultraviolet rays, but there are problems such as discoloration, skin irritation, pollution of the marine ecosystem, etc. Inorganic materials have a high refractive index and are not absorbed into the skin. Thus, they cause no side effects such as allergies, and there is an advantage of high skin safety. However, since inorganic materials have strong cohesiveness due to their nature, their feeling of use may be reduced due to an increase in size, and there is a problem in that white turbidity occurs when inorganic materials are excessively used to increase the blocking effect.

Inorganic materials have been mainly used as infrared ray-blocking materials. Large particles are used in infrared ray-blocking materials developed so far. They may be used by physically mixing with small particles or by coating with small particles. Most of them block both ultraviolet rays and infrared rays at the same time. However, due to agglomeration between inorganic materials of different sizes, there is a problem in that the effect of blocking ultraviolet rays and infrared rays is rather inhibited due to white turbidity caused by multiple scattering, non-uniformity in the coating process, etc.

DESCRIPTION OF EMBODIMENTS

Technical Problem

Accordingly, it is required to develop a cosmetic composition that is capable of effectively block ultraviolet rays and infrared rays at the same time by preventing agglomeration of the inorganic materials which block ultraviolet rays and infrared rays.

Solution to Problem

One aspect provides a cosmetic composition for blocking ultraviolet rays and infrared rays at the same time, the cosmetic composition including an inorganic material which blocks ultraviolet rays; an inorganic material which blocks infrared rays; and a dispersing agent.

Advantageous Effects of Disclosure

A cosmetic composition for blocking ultraviolet rays and infrared rays at the same time according to an aspect includes an inorganic material which blocks ultraviolet rays, an inorganic material which blocks infrared rays, and a dispersing agent at an appropriate ratio, thereby significantly blocking light in the ultraviolet and near-infrared regions and preventing skin aging caused by photoaging.

BEST MODE

Figure 1:
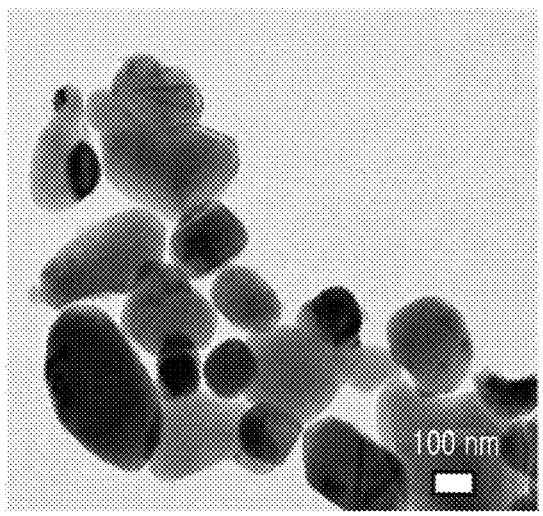
FIG. 1 shows transmission electron microscope images of an inorganic material which blocks ultraviolet rays (left) and an inorganic material which blocks infrared rays (right)
Figure 1:
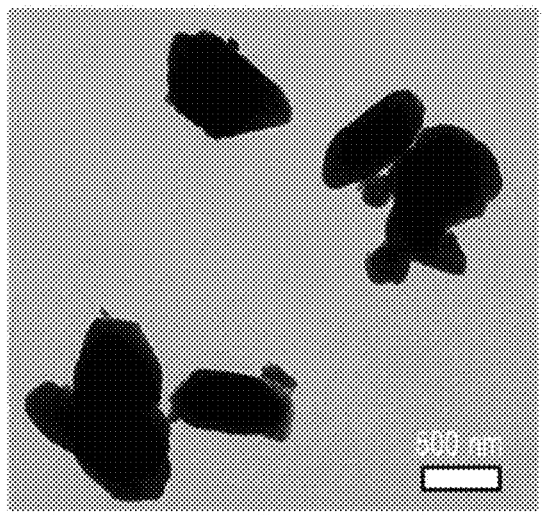

One aspect provides a cosmetic composition for blocking ultraviolet rays and infrared rays at the same time, the cosmetic composition including an inorganic material which blocks ultraviolet rays; an inorganic material which blocks infrared rays; and a dispersing agent.

As used herein, the term "inorganic material which blocks ultraviolet rays" refers to a material that reflects or scatters light in the ultraviolet region. The inorganic material which blocks ultraviolet rays may have a particle size of 100 nm to 500 nm.

The inorganic material which blocks ultraviolet rays may include all kinds of inorganic materials which blocks ultraviolet rays, which are generally included in cosmetic compositions. For example, the inorganic material which blocks ultraviolet rays may be titanium dioxide, zinc oxide, iron oxide, or a combination thereof. In one embodiment, it was confirmed that titanium dioxide having a size of 100 nm to 500 nm as the inorganic material which blocks ultraviolet rays exhibits a high sun protection factor.

The composition may include the inorganic material which blocks ultraviolet rays in an amount of 1% by weight to 25% by weight, for example, 1% by weight to 20% by weight, for example, 1% by weight to 18% by weight, for example, 1% by weight to 16% by weight, for example, 1% by weight to 15% by weight, for example, 1% by weight to 13% by weight, for example, 2% by weight to 12% by weight.

As used herein, the term "inorganic material which blocks infrared rays" refers to a material that reflects or scatters light in the infrared region, particularly, in the near-infrared region. The inorganic material which blocks infrared rays may have a particle size of 500 nm to 1500 nm.

The inorganic material which blocks infrared rays may include all kinds of inorganic materials which blocks infrared rays, which are generally included in cosmetic compositions. For example, the inorganic material which blocks infrared rays may be gold, silver, aluminum oxide, aluminum hydroxide, titanium dioxide, zinc oxide, iron oxide ($Fe_2O_3$), copper oxide ($CuO$, $CuO_2$), cerium oxide ($CeO_2$, $Ce_2O_3$), zirconium dioxide ($ZrO_2$), or a combination thereof. In one embodiment, it was confirmed that titanium dioxide having a size of 500 nm to 1500 nm as the inorganic material which blocks infrared rays exhibits a high sun protection factor.

The composition may include the inorganic material which blocks infrared rays in an amount of 1% by weight to 25% by weight, for example, 1% by weight to 20% by weight, for example, 1% by weight to 18% by weight, for example, 1% by weight to 16% by weight, for example, 1% by weight to 15% by weight, for example, 1% by weight to 13% by weight, for example, 2% by weight to 12% by weight.

As used herein, the term "dispersing agent" refers to a surfactant used to maintain a dispersion state in which solid particles are uniformly mixed in a liquid, and specifically, may refer to a material added to prevent agglomeration of large-sized particles and small-sized particles.

The dispersing agent may include all kinds of dispersing agents generally included in cosmetic compositions. The dispersing agent may be, for example, polyhydroxystearic acid, caprylic and capric triglyceride, isostearic acid, lecithin, polyglyceryl-3 polyricinoleate, or a combination thereof. In one embodiment, it was confirmed that when a combination of polyhydroxystearic acid, caprylic and capric triglyceride, isostearic acid, lecithin, and polyglyceryl-3 polyricinoleate is included as the dispersing agent, agglomeration of the inorganic material which blocks ultraviolet rays and the inorganic material which blocks infrared rays is prevented, a problem such as stiff feeling, white turbidity, etc. is improved, and high ultraviolet protection factor and infrared protection factor are achieved.

The composition may include a dispersing agent in an amount of 1% by weight to 15% by weight, for example, 1% by weight to 13% by weight, for example, 1% by weight to 12% by weight, for example, 1% by weight to 10% by weight, for example, 1% by weight to 8% by weight, for example, 1% by weight to 7% by weight, for example, 2% by weight to 7% by weight.

A weight ratio of the inorganic material which blocks ultraviolet rays, the inorganic material which blocks infrared rays, and the dispersing agent may be 3 to 7:3 to 7:1 to 5, for example, 1.5:1.5:1 to 3:3:1, for example, 2:2:1 to 3:3:1, for example, 1.5:1.5:1 to 4:4:1, for example, 2:2:1 to 4:4:1. In one embodiment, it was confirmed that when the inorganic material which blocks ultraviolet rays, the inorganic material which blocks infrared rays, and the dispersing agent are included at a weight ratio of 5:5:3, the effect of blocking ultraviolet rays and infrared rays at the same time, low white turbidity, high dispersibility, and improved feeling of use were observed. Therefore, when the weight ratio deviates from the above range, the effect of blocking ultraviolet rays and infrared rays at the same time may be unsatisfactory, or problems such as white turbidity and stiff feeling may occur due to agglomeration between the inorganic materials.

In addition to the above components, the cosmetic composition may further include, as needed, a stabilizer, a fragrance, an antioxidant, a thickener, a moisturizer, a softening agent, a high oil absorption powder, a viscosity lowering agent, a pH adjuster, etc., within a range that does not reduce the effects of the composition. In addition, the cosmetic composition may further include a substance that may supplementally provide essential nutrients for the skin, and specifically, may include an auxiliary agent including, but is not limited to, a natural fragrance, a cosmetic fragrance, or a plant extract.

The cosmetic composition may be prepared in any formulation commonly prepared in the art, for example, a solution, a suspension, an emulsion, a paste, a gel, a cream, a lotion, a powder, an oil, a powder foundation, an emulsion foundation, a wax foundation, a spray, etc., but is not limited thereto. More specifically, it may be prepared in the formulation of a sun block cream, a softening lotion, an astringent lotion, a nourishing lotion, a nourishing cream, a massage cream, an essence, an eye cream, a pack, a spray, or a powder.

MODE OF DISCLOSURE

Hereinafter, the present disclosure will be described in more detail with reference to exemplary embodiments. However, these exemplary embodiments are only for illustrating, and the scope of the present disclosure is not limited to these exemplary embodiments.

COMPARATIVE EXAMPLES 1 to 3 AND EXAMPLES 1 and 2 PREPARATION OF COSMETIC COMPOSITION FOR BLOCKING ULTRAVIOLET RAYS AND INFRARED RAYS AT THE SAME TIME Cosmetic compositions of Comparative Examples 1 to 3 and Examples 1 and 2 were prepared by varying including of an inorganic material which blocks ultraviolet rays, an inorganic material which blocks infrared rays, and a dispersing agent. Components and contents (wt %) of the cosmetic compositions of Comparative Examples 1 to 3 and Examples 1 and 2 are shown in Table 1 below.

TABLE 1

| Section | Components | Comparative Example 1 | Comparative Example 2 | Comparative Example 3 | Example 1 | Example 2 |
|---|---|---|---|---|---|---|
| Oil phase | Lauryl PEG-polydimethylsiloxyethyl dimethicone | 1.00 | 1.00 | 1.00 | 1.00 | 1.00 |
| | PEG-10 dimethicone | 3.00 | 3.00 | 3.00 | 3.00 | 3.00 |
| | Ethylhexyl methoxycinnamate | 5.00 | 5.00 | 5.00 | 5.00 | 5.00 |
| | Butylene glycol dicaprylate/dicaprate | 3.00 | 3.00 | 3.00 | 3.00 | 3.00 |
| | Diphenylsiloxy phenyl trimethicone | 2.00 | 2.00 | 2.00 | 2.00 | 2.00 |

TABLE 1-continued

| Section | Components | Comparative Example 1 | Comparative Example 2 | Comparative Example 3 | Example 1 | Example 2 |
|---|---|---|---|---|---|---|
| | Cyclopentasiloxane | 5.00 | 5.00 | 5.00 | 5.00 | 5.00 |
| | Cyclohexasiloxane Dimethicone | 5.00 | 5.00 | 5.00 | 5.00 | 5.00 |
| | Disteardimonium hectorite | 0.50 | 0.50 | 0.50 | 0.50 | 0.50 |
| Inorganic material | Titanium dioxide (Ultraviolet ray-blocking inorganic material) | 5.00 | — | 5.00 | 5.00 | 10.00 |
| | Titanium dioxide (Near-infrared ray-blocking inorganic material) | — | 5.00 | 5.00 | 5.00 | 10.00 |
| Dispersing agent | Polyhydroxystearic acid/Caprylic/Capric triglyceride/Isostearic acid/Lecithin/Polyglyceryl-3 polyricinoleate | — | — | — | 3.00 | 6.00 |
| Aqueous phase | Purified water | To 100 | To 100 | To 100 | To 100 | To 100 |
| | Disodium EDTA | 0.02 | 0.02 | 0.02 | 0.02 | 0.02 |
| | Polyol | 5.00 | 5.00 | 5.00 | 5.00 | 5.00 |
| | Preservative | Appropriate amount | Appropriate amount | Appropriate amount | Appropriate amount | Appropriate amount |
| Total | | 100 | 100 | 100 | 100 | 100 |

In detail, the compositions of Comparative Examples 1 to 3 were prepared by dispersing an inorganic material by mixing with an oil phase, and dissolving by heating to 70° C. to 80° C. Thereafter, an aqueous phase was added, followed by stirring. The compositions of Examples 1 and 2 were prepared by dispersing the inorganic material which blocks ultraviolet rays and the inorganic material which blocks infrared rays in the dispersing agent, mixing them with the oil phase, and dissolving by heating to 70° C. to 80° C. Then, the aqueous phase was added and stirred to prepare the compositions. The compositions of Comparative Examples 1 and 2 were those prepared to include only one of the inorganic material which blocks ultraviolet rays and the inorganic material which blocks infrared rays, and the composition of Comparative Example 3 was prepared by simply mixing the inorganic material which blocks ultraviolet rays and the inorganic material which blocks infrared rays. In contrast, the compositions of Examples 1 and 2 were prepared by further including the dispersing agent described in Table 1, and by mixing the inorganic material which blocks ultraviolet rays and the inorganic material which blocks infrared rays.

EXPERIMENTAL EXAMPLE 1. EXAMINATION OF PARTICLE SIZE OF INORGANIC MATERIAL

To compare particle sizes of the inorganic material which blocks ultraviolet rays and the inorganic material which blocks infrared rays included in the compositions of Examples 1 and 2, transmission electron microscopy (TEM) images were photographed.

As a result, as shown in FIG. 1, it was confirmed that the inorganic material which blocks ultraviolet rays exhibited a particle size of 100 nm to 500 nm (left image), whereas the inorganic material which blocks infrared rays exhibited a particle size of 500 nm to 1500 nm (right image).

EXPERIMENTAL EXAMPLE 2. EXAMINATION OF EFFECT OF BLOCKING ULTRAVIOLET RAYS

Sun protection factors (SPFs) of the cosmetic compositions of Comparative Examples 1 to 3 and Examples 1 and 2 were evaluated. SPFs of the cosmetic compositions of Comparative Examples 1 to 3 and Examples 1 and 2 are shown in Table 2 below.

In detail, to evaluate the effect of blocking ultraviolet rays, in vitro SPF was measured using a Labsphere UV-2000S which is an in vitro sunscreen analyzer. For in vitro SPF measurement, each sample was uniformly applied onto an optical PMMA plate suitable for UV transmittance measurement, and then ultraviolet rays (290 nm to 400 nm) were irradiated using the measurement device to measure in vitro SPF. At this time, each sample was measured in triplicate.

TABLE 2

| | Comparative Example 1 | Comparative Example 2 | Comparative Example 3 | Example 1 | Example 2 |
|---|---|---|---|---|---|
| Sun protection factor (SPF) | 40.65 | 16.69 | 31.00 | 41.89 | 48.39 |

As a result, as shown in Table 2, the composition of Comparative Example 1 including the inorganic material which blocks ultraviolet rays exhibited a high sun protection factor, whereas the composition of Comparative Example 2 including only the inorganic material which blocks infrared rays exhibited a low sun protection factor. In addition, the composition of Comparative Example 3, which included both the inorganic material which blocks ultraviolet rays and the inorganic material which blocks infrared rays, but was prepared by simple mixing thereof, exhibited a disadvantage of the low sun protection factor due to agglomeration between the two inorganic materials. In contrast, the compositions of Examples 1 and 2 exhibited high sun protection factors by further including a dispersing agent in an appropriate ratio even though they included two kinds of inorganic materials. The sun protection factors also increased as the content of the inorganic materials increased.

EXPERIMENTAL EXAMPLE 3. EXAMINATION OF EFFECT OF BLOCKING INFRARED RAYS

Infrared protection factor (IPFs) of the cosmetic compositions of Comparative Examples 1 to 3 and Examples 1 and 2 were evaluated. IPFs of the cosmetic compositions of Comparative Examples 1 to 3 and Examples 1 and 2 are shown in Table 3 below.

In detail, the following clinical evaluation method developed by the present inventors was used. The effect of blocking infrared rays was evaluated by measuring spectral reflectance at the wavelength of the near-infrared region, and an instrument used for the measurement was a near-infrared ray spectrophotometer (NIR Spectrophotometer, ASD Inc., USA). The results were measured from 5 people for each sample, and the mean value thereof was shown.

[Method of evaluating effect of blocking near-infrared rays]

1) Preparing a size of 3.5×3.5 cm on the skin inside the human arm
2) Measuring spectral reflectance before sample application (control)
3) Evenly applying 2 µL/cm² of the sample using your finger
4) Leaving for 15 minutes
5) Measuring spectral reflectance where the sample was applied (sample)
6) Measuring the effect of blocking infrared rays by putting the spectral reflectance before and after application of the sample in the following equation (IPF: Infrared Protection Factor)

$$IPF = \frac{\int_{760\,nm}^{1400\,nm} \text{Reflectance (sample)} - \int_{760\,nm}^{1400\,nm} \text{Reflectance (control)}}{\int_{760\,nm}^{1400\,nm} \text{Reflectance (control)}} \times 100 \quad \text{[Equation 1]}$$

The higher the IPF, the higher the reflectance of near-infrared rays reaching the skin, which means that it is more effective in blocking near-infrared rays. Accordingly, it was examined how high the spectral reflectance after application of the sample was as compared to that before application.

TABLE 3

|  | Comparative Example 1 | Comparative Example 2 | Comparative Example 3 | Example 1 | Example 2 |
|---|---|---|---|---|---|
| Infrared protection factor (IPF) | 12.17 | 16.30 | 18.27 | 20.80 | 24.90 |

As a result, as shown in Table 3, the composition of Comparative Example 1 including no inorganic material which blocks infrared rays showed a low infrared protection factor, as compared with the composition of Comparative Example 2 including the inorganic material which blocks infrared rays. The composition of Comparative Example 3 including both the inorganic material which blocks ultraviolet rays and the inorganic material which blocks infrared rays exhibited an increased infrared protection factor, as compared with the compositions of Comparative Examples 1 and 2. However, the compositions of Examples 1 and 2, which were prepared not by simply mixing the two inorganic materials like the composition of Comparative Example 3, but by further including a dispersing agent at an appropriate ratio, exhibited an increased infrared protection factor. As the content of the inorganic materials increased, the sun protection factor also increased. The above results confirmed that the compositions of Examples 1 and 2 further include the dispersing agent to stably disperse the inorganic materials in the formulation even including both the inorganic materials having different sizes, thereby exhibiting the better effect of blocking ultraviolet rays and infrared rays.

EXPERIMENTAL EXAMPLE 4. EVALUATION OF WHITE TURBIDITY OF COSMETIC COMPOSITION

White turbidity (whiteness) of the cosmetic compositions of Comparative Examples 1 to 3 and Examples 1 and 2 were evaluated. White turbidity values (L values) of the cosmetic compositions of Comparative Examples 1 to 3 and Examples 1 and 2 are shown in Table 4 below.

In detail, after each cosmetic composition was applied to a rectangular black artificial leather of 2×2 cm², the L value was measured using a spectrophotometer (Minolta CM-2600d). 8 µL of each sample was applied, and rubbed with a finger 10 times. 2 minutes later, the L value of each sample was compared using the spectrophotometer. The smaller L value means the lower white turbidity.

TABLE 4

|  | Comparative Example 1 | Comparative Example 2 | Comparative Example 3 | Example 1 | Example 2 |
|---|---|---|---|---|---|
| White turbidity (L value) | 43.02 | 33.84 | 50.77 | 32.50 | 36.62 |

As a result, as shown in Table 4, the composition of Comparative Example 1 including only the inorganic material which blocks ultraviolet rays showed a high white turbidity, whereas the composition of Comparative Example 2 including only the inorganic material which blocks infrared rays showed a low white turbidity. In addition, the composition of Comparative Example 3, in which the inorganic material which blocks ultraviolet rays and the inorganic material which blocks infrared rays were simply mixed, showed a significantly increased white turbidity due to agglomeration between the inorganic materials. In contrast, the compositions of Examples 1 and 2, each further including the dispersing agent at an appropriate ratio in addition to the two inorganic materials, showed a significantly low white turbidity, as compared with the composition of Comparative Example 3. The above results indicate that when the dispersing agent is further included in the cosmetic compositions including both the inorganic material which blocks ultraviolet rays and the inorganic material which blocks infrared rays, agglomeration between the inorganic materials is prevented to exhibit the low white turbidity, and thus various formulations of the cosmetic compositions may be prepared.

EXPERIMENTAL EXAMPLE 5. EVALUATION OF DISPERSIBILITY OF COSMETIC COMPOSITION

The dispersibility of the cosmetic compositions of Comparative Examples 1 to 3 and Examples 1 and 2 was evaluated through microscopic observation.

Figure 2:
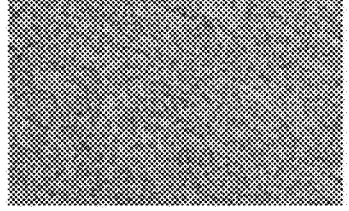
FIG. 2 shows observation by a microscope to evaluate dispersibility of compositions of Comparative Examples 1 to 3 and Experimental Examples 1 and 2.
Figure 2:
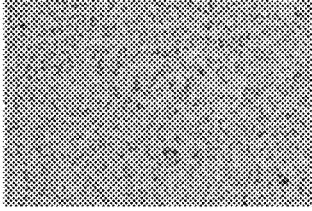
Figure 2:
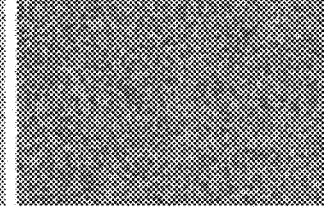
Figure 2:
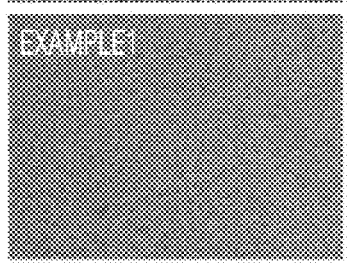
Figure 2:
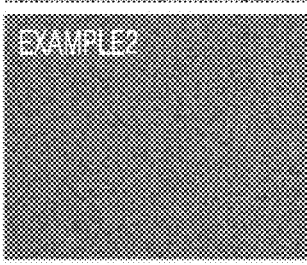

As a result, as shown in FIG. 2, the cosmetic compositions of Comparative Example 1 to Comparative Example 3 showed that particles were agglomerated or not evenly distributed. In particular, it was confirmed that the composition of Comparative Example 3 had the largest particle agglomerate due to agglomeration between the inorganic materials. In contrast, it was confirmed that the compositions of Examples 1 and 2 further included the dispersing agent at an appropriate ratio to prevent agglomeration between the inorganic material which blocks ultraviolet rays and the inorganic material which blocks infrared rays, thereby showing the evenly distributed particles.

EXPERIMENTAL EXAMPLE 6. EVALUATION OF FEELING OF USE OF COSMETIC COMPOSITION

The feeling of use of the cosmetic compositions of Comparative Example 3, Examples 1 and 2, each including both the inorganic material which blocks ultraviolet rays and the inorganic material which blocks infrared rays was evaluated. The evaluation results are shown in Table 4 below.

In detail, 20 adult males and females without skin diseases were asked to use the cosmetic composition on the face and cheeks. Since cosmetic compositions including the inorganic materials have serious problems of stiff feeling or high degree of white turbidity when applied to the skin, texture (stiff feeling), white turbidity, and overall satisfaction of the cosmetic compositions were evaluated. The evaluation results were marked as ⊚ when 15 or more people were satisfied, ○ when 10 or more people were satisfied, and Δ when 5 or more people were satisfied.

TABLE 5

|  | Comparative Example 3 | Example 1 | Example 2 |
|---|---|---|---|
| Texture (stiff feeling) | Δ | ⊚ | ⊚ |
| White turbidity | Δ | ○ | ○ |
| Overall satisfaction | Δ | ⊚ | ⊚ |

As a result, as shown in Table 5, the composition of Comparative Example 3, in which the inorganic material which blocks ultraviolet rays and the inorganic material which blocks infrared rays were physically mixed, exhibited not only a non-smooth formulation appearance, but also stiff texture. In contrast, the compositions of Examples 1 and 2, in which the inorganic material which blocks ultraviolet rays and the inorganic material which blocks infrared rays were mixed using the dispersing agent, exhibited remarkable improvement in stiff texture and white turbidity, indicating that the overall satisfaction for feeling of use is high.

The above results suggest that when the cosmetic composition for blocking ultraviolet rays and infrared rays at the same time includes the inorganic material which blocks ultraviolet rays, the inorganic material which blocks infrared rays, and the dispersing agent which are appropriately mixed, agglomeration between the two inorganic materials is effectively prevented, thereby exhibiting the effects of blocking ultraviolet rays and infrared rays at the same time and also solving the problems such as white turbidity and stiff texture.

The invention claimed is:

1. A cosmetic composition for blocking ultraviolet rays and infrared rays at the same time, the cosmetic composition comprising an inorganic material which blocks ultraviolet rays; an inorganic material which blocks infrared rays; and a dispersing agent, wherein a weight ratio of the inorganic material which blocks ultraviolet rays, the inorganic material which blocks infrared rays, and the dispersing agent is 1.5:1.5:1 to 3:3:1.

2. The cosmetic composition of claim 1, wherein the inorganic material which blocks ultraviolet rays has a particle size of 100 nm to 500 nm; and the inorganic material which blocks infrared rays has a particle size of 500 nm to 1500 nm.

3. The cosmetic composition of claim 1, wherein the inorganic material which blocks ultraviolet rays is titanium dioxide, zinc oxide, iron oxide, or a combination thereof.

4. The cosmetic composition of claim 1, wherein the inorganic material which blocks infrared rays is gold, silver, aluminum oxide, aluminum hydroxide, titanium dioxide, zinc oxide, iron oxide, copper oxide, cerium oxide, zirconium dioxide, or a combination thereof.

5. The cosmetic composition of claim 1, wherein the dispersing agent is polyhydroxystearic acid, caprylic and capric triglyceride, isostearic acid, lecithin, polyglyceryl-3 polyricinoleate, or a combination thereof.

* * * * *